United States Patent [19]

Williams et al.

[11] Patent Number: 5,546,646
[45] Date of Patent: Aug. 20, 1996

[54] METHOD FOR MOUNTING AN INTRAVASCULAR STENT ON A CATHETER

[75] Inventors: Michael S. Williams, Chapel Hill, N.C.; Lilip Lau, Sunnyvale; Farhad Khosravi, Belmont; William Hartigan, Fremont; Avegel Hernando, Union City, all of Calif.

[73] Assignee: Advanced Cardiovascular Systems, Inc., Santa Clara, Calif.

[21] Appl. No.: 390,096

[22] Filed: Feb. 17, 1995

Related U.S. Application Data

[62] Division of Ser. No. 66,707, May 24, 1993, Pat. No. 5,437,083.

[51] Int. Cl.[6] ................................................. B23P 11/00
[52] U.S. Cl. ........................ 29/407.08; 29/282; 29/516
[58] Field of Search .............................. 29/234, 235, 280, 29/282, 283, 283.5, 407, 516, 517, 715, 407.08; 606/1, 151, 201; 81/418

[56] References Cited

U.S. PATENT DOCUMENTS

| 696,289 | 3/1902 | Williams | 29/235 |
|---|---|---|---|
| 4,070,745 | 1/1978 | Schimmelman | 81/418 X |
| 4,353,240 | 10/1982 | Undin et al. | 81/418 X |
| 4,907,336 | 3/1990 | Gianturco | 29/515 |
| 4,961,291 | 10/1990 | Lagassee | 81/418 X |
| 5,132,066 | 7/1992 | Charlesworth et al. | 264/184 |
| 5,133,732 | 7/1992 | Wiktor | 606/195 |
| 5,183,085 | 2/1993 | Timmermans | 140/89 |
| 5,189,786 | 3/1993 | Ishikawa et al. | 29/825 |

FOREIGN PATENT DOCUMENTS

| 159065 | 2/1921 | United Kingdom . |

*Primary Examiner*—S. Thomas Hughes
*Attorney, Agent, or Firm*—Fulwider Patton Lee & Utecht

[57] ABSTRACT

The method for mounting an intravascular stent on the distal end of a catheter. The stent-loading device includes at least two substantially flat surfaces, that are parallel to each other, and that have relative sliding movement while remaining parallel. A stent is placed on the distal end of a catheter and positioned between the substantially flat surfaces which are then moved in an orthogonal direction relative to each other while simultaneous compressive force is applied to the stent. The stent is progressively crimped onto the catheter.

6 Claims, 3 Drawing Sheets

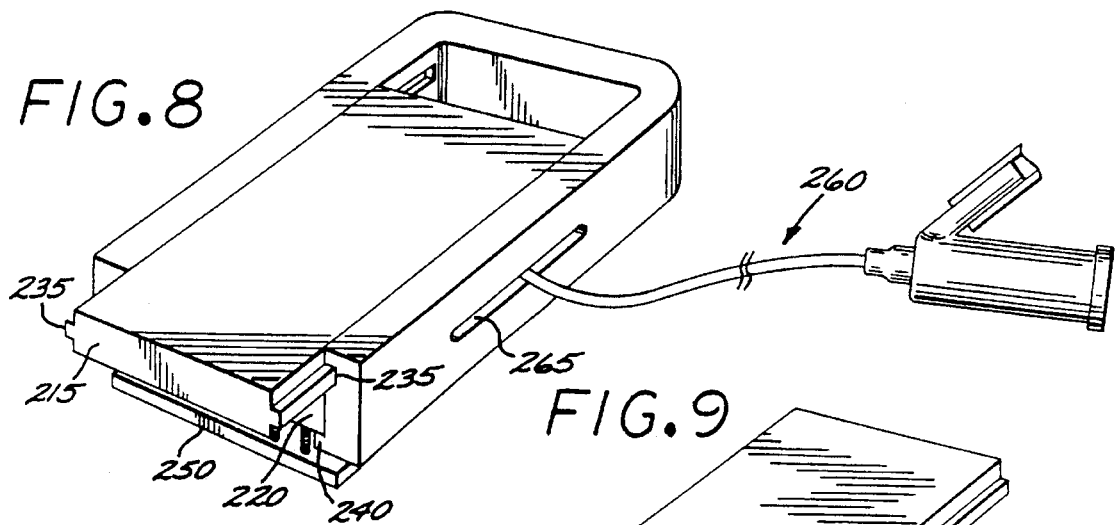
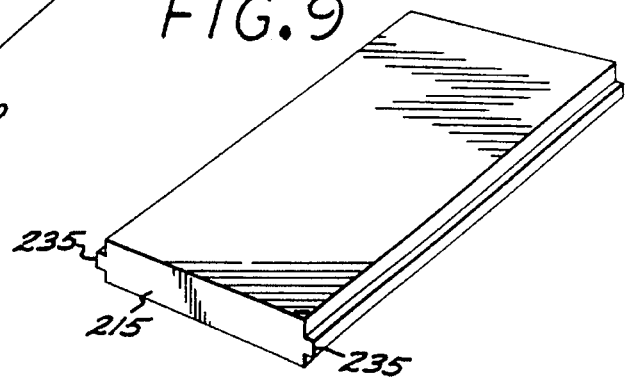
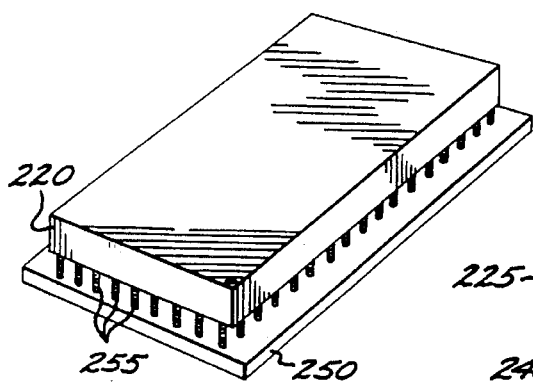
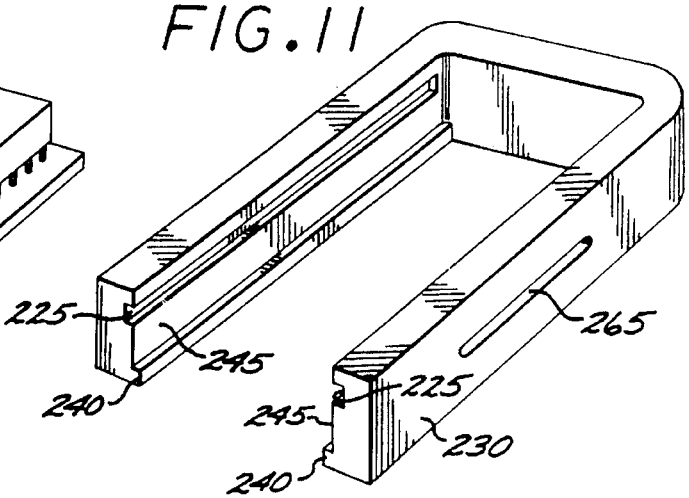

METHOD FOR MOUNTING AN INTRAVASCULAR STENT ON A CATHETER

This application is a division of U.S. Ser. No. 08/066,707, filed May 24, 1993, now U.S. Pat. No. 5,437,083.

BACKGROUND OF THE INVENTION

1. Field of the Invention

This invention relates to a stent loading device that will automatically load a stent onto the distal end of a balloon dilatation catheter assembly, for example, of the kind used in typical percutaneous transluminal coronary angioplasty (PTCA) procedures.

In typical PTCA procedures, a guiding catheter is percutaneously introduced into the cardiovascular system of a patient through the brachial or femoral arteries and advanced through the vasculature until the distal end is in the ostium. A guidewire and a dilatation catheter having a balloon on the distal end are introduced through the guiding catheter with the guidewire sliding within the dilatation catheter. The guidewire is first advanced out of the guiding catheter into the patient's coronary vasculature and the dilatation catheter is advanced over the previously advanced guidewire until the dilatation balloon is properly positioned across the lesion. Once in position across the lesion, a flexible, expandable, preformed balloon is inflated to a predetermined size with radiopaque liquid at relatively high pressures to radially compress the atherosclerotic plaque of the lesion against the inside of the artery wall and thereby dilate the lumen of the artery. The balloon is then deflated to a small profile, so that the dilatation catheter can be withdrawn from the patient's vasculature and blood flow resumed through the dilated artery. As should be appreciated by those skilled in the art, while the procedure just described is typical, it is not the only method used in angioplasty.

In angioplasty procedures of the kind referenced above, there may be restenosis of the artery, which may require another angioplasty procedure, a surgical bypass operation, or some method of repairing or strengthening the area. To reduce the chance of restenosis and strengthen the area, a physician can implant an intravascular prosthesis for maintaining vascular patency, typically called a stent, inside the artery at the lesion. The stent is typically expanded to a larger diameter, often by the balloon portion of the catheter. The stent may be of the self-expanding type.

SUMMARY OF THE INVENTION

This invention is directed to a vascular prosthesis loading device, which automatically loads a stent onto the distal end of a catheter assembly, with a minimum of human handling, to better secure the stent onto the catheter while the stent is being delivered through the patient's vasculature.

The present invention attempts to solve several problems associated with placing stents onto balloon catheters. In procedures where the stent is placed over the balloon portion of the catheter, one must crimp the stent onto the balloon portion, to prevent the stent from sliding off the catheter when the catheter is advanced in a patient's vasculature. In the past this crimping was often done by hand, which was found to be unsatisfactory due to uneven force being applied, resulting in non-uniform crimps. In addition, it is difficult to judge when a uniform and reliable crimp has been applied. Furthermore, the more the stent is handled, the greater the chance of human error in crimping the stent properly. Though some tools, such as ordinary pliers, have been used to apply the stent, these tools have not been entirely adequate in achieving a satisfactory crimp. Further, some self-expanding stents are difficult to load by hand onto a delivery device such as a catheter.

In one embodiment of the present invention, the stent loading device includes a tubular member housing a bladder. The tubular member and bladder are designed to hold a stent that is to be loaded onto a balloon catheter assembly. Upon placement of the stent over the balloon portion of the catheter, a valve in the loading device is activated to inflate the bladder. The bladder compresses the stent radially inwardly to a reduced diameter onto the balloon portion of the catheter, to achieve a snug fit. In this way the stent can be affixed onto the distal end of a balloon catheter with a minimum of human handling.

In other embodiments of the present invention, the stent loading device is made of sliding plates having flat surfaces that allow a stent carrying catheter to be received in between them. The surfaces are moved relative to one another to apply force uniformly to the outside of the stent disposed on the catheter, allowing the stent to be crimped onto the outside of the catheter.

These and other advantages of the invention will become more apparent from the following detailed description thereof when taken in conjunction with the accompanying drawings.

BRIEF DESCRIPTION OF THE DRAWINGS

FIG. 8 is a perspective view of a third embodiment of the present invention.

FIG. 9 shows the slider plate of the embodiment of FIG. 8.

FIG. 10 shows the spring loaded plate of the embodiment of FIG. 8.

FIG. 11 shows the housing of the embodiment of FIG. 8.

DETAILED DESCRIPTION OF THE INVENTION

Figure 1:
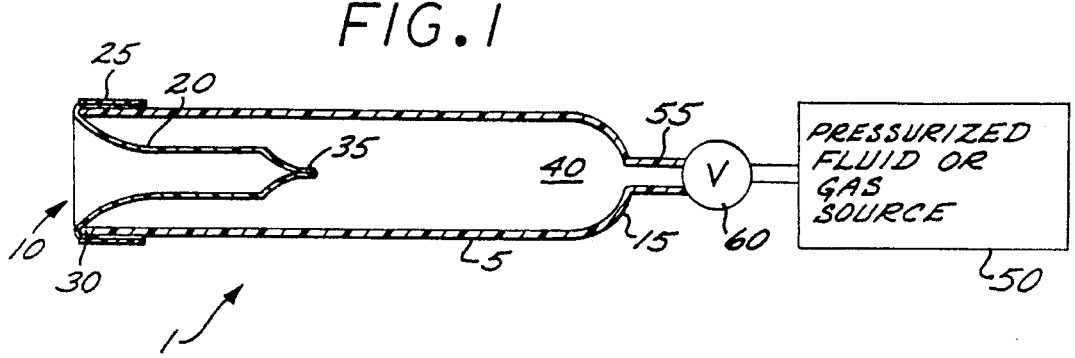
FIG. 1 is a cross-sectional schematic of one embodiment of the stent loading device depicting the bladder and chamber for receiving the stent.
Figure 2:
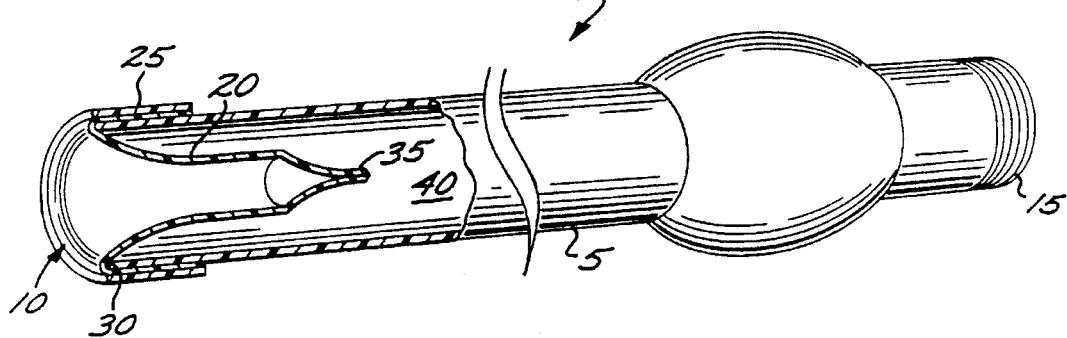
FIG. 2 is a cut away perspective view of the stent loading device of FIG. 1.

As shown by FIGS. 1–4, the first embodiment of the stent loading device 1 includes an elongated tubular member 5, having an open end 10 and a sealed off end 15. The tubular member houses an elastic bladder 20, which extends longitudinally along the inside of the tubular member. The bladder is secured to the tubular member by fastener ring 25, which clamps the bladder onto the tubular member. The bladder extends out of the open end of the tubular member and is folded over outside end 30 of the tubular member.

The tubular member can be made of a stainless steel or polytetrafluoroethylene (Teflon™) lined hypotube. The bladder can be made of any flexible, elastic material, such as polyethylene material.

The bladder is sealed at its end 35. The bladder end may be sealed by heat sealing, by an adhesive, by tying, or by clamping with a hemostat, depending on the bladder material used. As shown in the figures, the bladder seals from atmosphere an annular fluid chamber 40 in the tubular member. Chamber 40 can be placed under pressure by a pressurized fluid source 50, which is in fluid communication with the chamber via inflation port 55 fitted with an inflation valve 60. In the preferred embodiment an adaptor with a male threaded Luer fitting is used as an inflation port. A syringe, indeflator, compressed fluid source or other pressurizing means 50 is attached to the inflation port.

Operation of the stent loading device of FIGS. 1–4 will now be described. When it is desired to load a stent 65 onto a balloon catheter assembly 70, a stent is inserted inside the open end 10 of the tubular member 5. The stent is confined inside the tubular member by the inner walls of the bladder, with the bladder being in a deflated state. The collapsed balloon portion 85, adjacent distal end 90 of the balloon catheter 95, is inserted inside the stent so the stent overlies the balloon portion. At this point there is no pressure inside the sealed fluid chamber 40.

Figure 3:
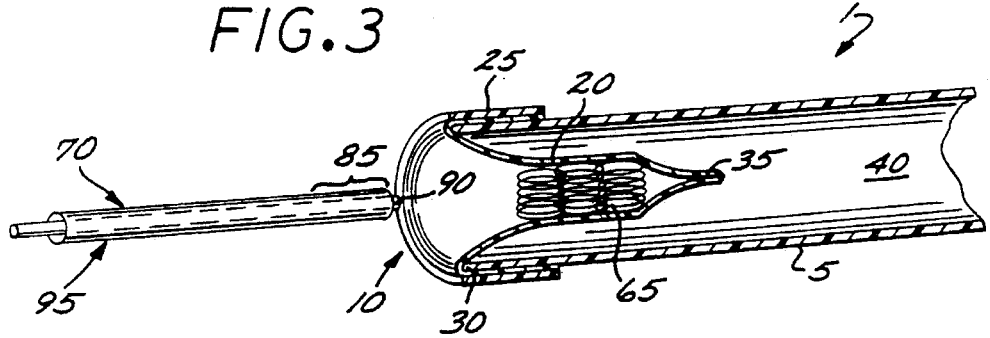
FIG. 3 is a cut away perspective view of the stent loading device of FIG. 1, showing a balloon catheter assembly about to be inserted into the device, and a stent received by the device.
Figure 4:
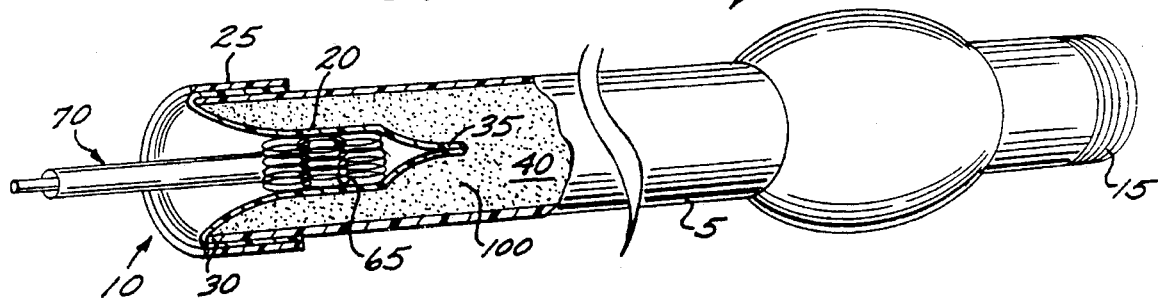
FIG. 4 is a cut away perspective view of the stent loading device of FIG. 1, when it is operated to load a stent onto a balloon catheter assembly that has been placed inside the device.

To load and attach the stent onto the balloon portion of the catheter assembly, the catheter is brought into operating engagement with the stent loading device. The catheter has been checked and prepped before this time, and the profile of the balloon portion 85 has been reduced to its minimum. As illustrated in FIG. 3, the catheter is inserted with its distal end first into open end 10 of the tubular member. To achieve insertion, the balloon catheter assembly may be held stationary while the stent delivery device is moved relative to the catheter. The catheter distal end is inserted far enough into the tubular member so the stent is positioned over the desired position on the catheter. At this point the stent is not fixed onto the balloon catheter assembly, because the stent has not been compressed.

The stent is attached onto the balloon 85 of catheter 95 by first pressurizing chamber 40. As chamber 40 is pressurized, tubular member 5 becomes pressurized, and the pressure is transferred to the bladder, which causes it to inflate and compress radially inwardly the stent onto the balloon portion of the catheter, at a substantially uniform rate. The inflation of the chamber is depicted by dotted shading in FIG. 4. Pressurized fluid may be introduced into chamber 40 through inflation port 55 controlled by a suitable valve 60 by way of a compressed fluid source 50, as shown in FIG. 1. The fluid may also be introduced by way of a syringe or plunger arrangement, such as an indeflator. Other suitable pressurizing gas or fluid sources are contemplated, as should be appreciated by one skilled in the art.

After a predetermined pressure has been achieved and the stent has been affixed to the outside of the balloon portion of the balloon catheter assembly, the bladder 10 is deflated by releasing the pressurized air from inside the chamber through valve 60. Tubular member 5 is then withdrawn from over the catheter assembly. The delivery catheter, now loaded with a stent, is ready to be inserted into the body of a patient for deployment.

Furthermore, the stent loading device of FIGS. 1–4 may be used to compress and affix a stent that has been first manually placed over a balloon catheter.

Figure 5:
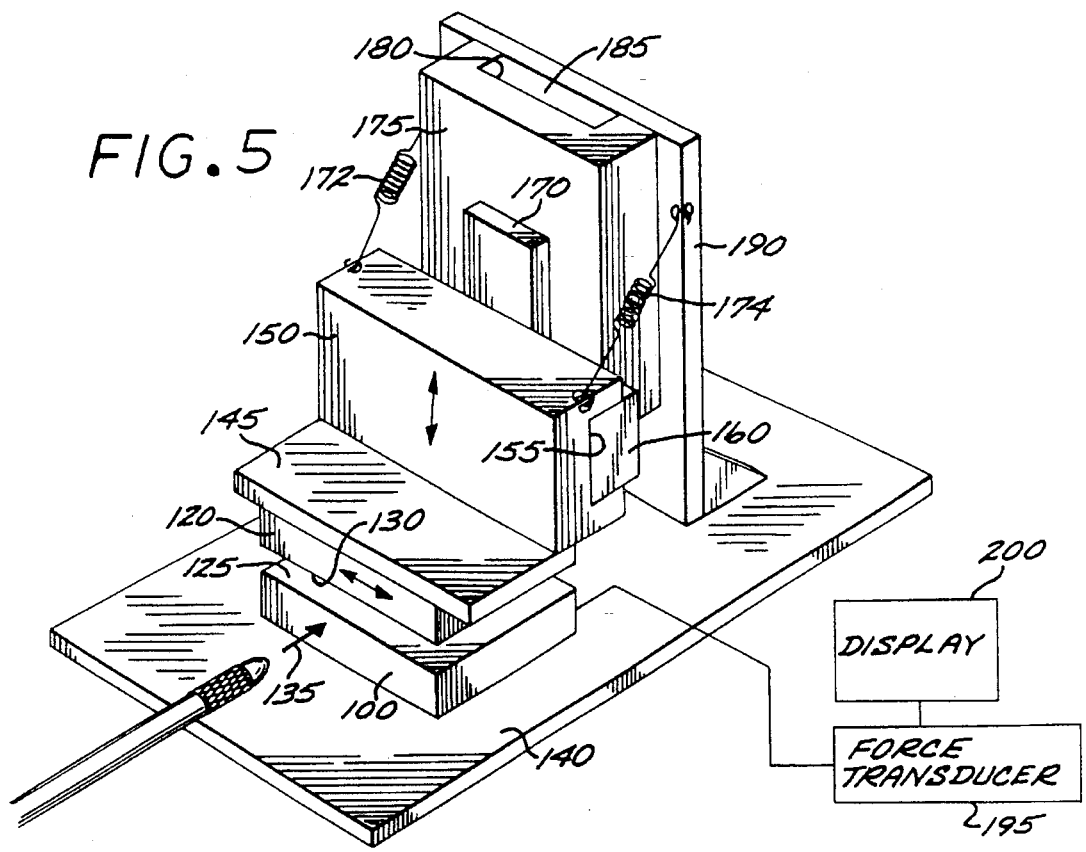
FIG. 5 is a perspective view of a second embodiment of the present invention depicting sliding plates with a stent mounted between the plates.
Figure 6:
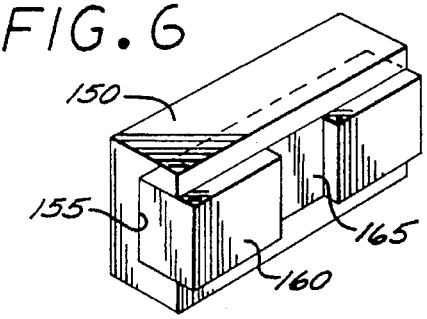
FIG. 6 is a perspective view of the back of one of the blocks of the embodiment shown in FIG. 5.
Figure 7:
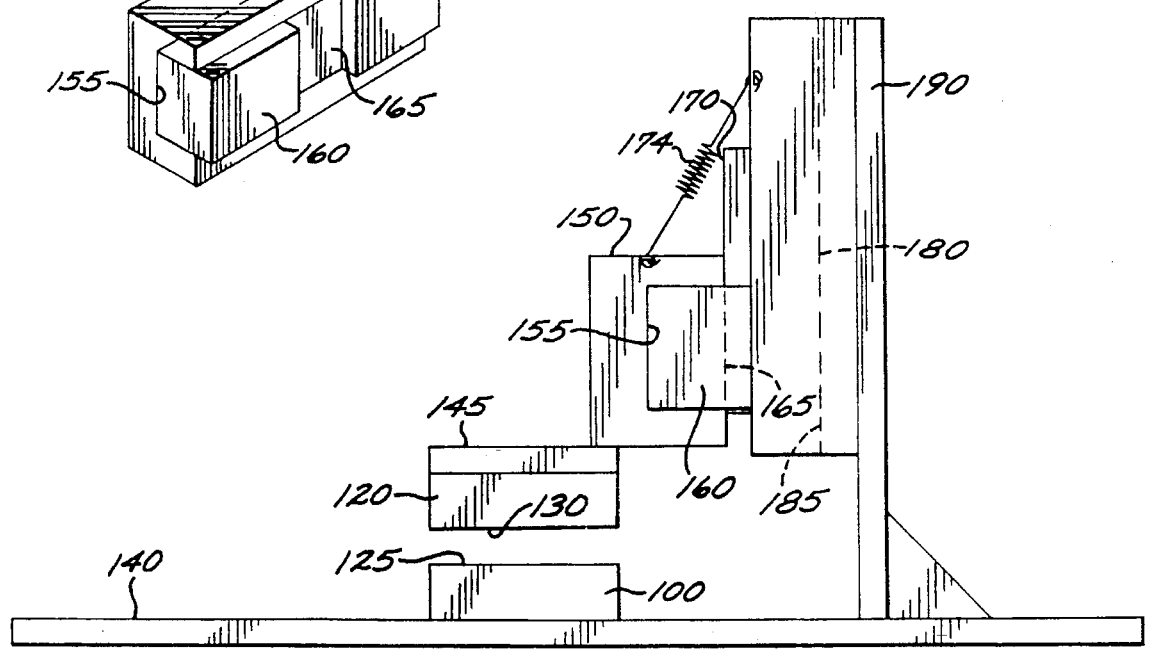
FIG. 7 is a side view of the second embodiment of the present invention.

Turning attention now to the embodiment of FIGS. 5–7, there is shown a second embodiment of the present invention. In FIG. 5 there is shown an isometric perspective view of the device. The device comprising a pair of plates, a lower support plate 100 and an upper support plate 120, that form flat surfaces or faces 125, 130, in between which a stent carrying catheter may be placed, as indicated by arrow 135. Uniform pressure may be applied to crimp the stent onto the catheter, by reciprocating surfaces 125, 130 relative to one another. Plates 100, 120 may be made of aluminum, and may be hollow. Thin rubber or elastomeric surfaces are laminated onto faces 125, 130 to better grip the stent and catheter and prevent them from sliding. The upper face 130 has a thicker rubber or elastomeric surface, about ¾" thick, and the lower face 125 has a thinner rubber surface, about ¼" thick.

Lower support plate 100 is fixed to base 140 while upper support plate 120 is movable, being affixed to flat rectangular surface 145 which in turn is affixed to channel-shaped block 150. Channel-shaped block 150 translates in two directions. Channel shaped block 150 has a horizontally extending channel or groove 155 extending along its length through which it slidably receives a guide bearing surface 160. Guide bearing surface 160 in turn has a vertically extending channel or groove 165 on its back side, as can be seen in FIG. 6, which receives a rail 170. Rail 170 is fixed to upright channel shaped support 175. Upright channel support 175 in turn has a groove 180 that can slidably receive a fixed rail 185. Fixed rail 185 is immobile, fixed to a vertical post 190, which is attached to base 140.

Spring arms 172, 174 provide bias along the axial direction (the direction of arrow 135) to keep block 150, guide bearing surface 160 and rail 170 together. In addition spring arms 172, 174 provide a vertical bias to keep faces 125, 130 separated.

As can be appreciated from an examination of FIGS. 5–7, guide bearing surface 160 allows two degrees of freedom for the translation of plate 120, that is, allowing for movement along vertical and horizontal directions. Preferably these directions are substantially orthogonal directions, that is, at right angles to one another, as shown by the unmarked double headed arrows in FIG. 5.

Furthermore, the use of several redundant sliding surfaces, such as guide bearing surface 160 in conjunction with channel shaped support 175, both sliding along rails in the vertical direction, allows for reduced friction in the event there is excessive friction along one sliding surface. Multiple sliding surfaces may be employed for horizontal travel as well.

Furthermore, upper block 150 is spring biased upwards from lower support plate 100 by spring arms 172, 174. The arms provide for the upper block 150 to be spaced from lower support plate 100, and to give a resilient feel to an operator pressing down on upper block 150. The spring biased arms may have spring tensioning means to adjust the spring tension in the arms, as well as dampening means for providing dampening.

In addition, a force transducer 195, such as a strain gage or piezoelectric crystal, may be disposed in plate 100 and/or plate 120, or in faces 125, 130, to measure the contact force applied to the stent disposed between the plates. Force transducer 195 may have a display 200, giving visual and/or audio output, to provide feedback to the operator and to indicate when either sufficient and/or excessive force has been imparted to the catheter.

Operation of the FIGS. 5–7 embodiment is achieved by placing a catheter that has a stent disposed about its stent receiving portion, which in a balloon catheter would be the balloon portion of the catheter, in between the space formed between the substantially flat surfaces of faces 125, 130. The operator then gently reciprocates plate 120 to move face 130, which contacts the stent receiving catheter, with respect to face 125, which is fixed and also contacts the catheter, to apply a slight downward force and evenly crimp the stent onto the catheter. The gentle reciprocating motion of the two substantially flat rubberized faces 125, 130, together with the downward application of force, insures an even application of force to the outside of the stent and achieves a uniform crimping of the stent onto the catheter.

Turning attention now to FIGS. 8–11, there is shown another embodiment of the present invention employing sliding plates that operate in principle according to the embodiment of FIG. 5. A horizontally sliding plate 215 moves relative to a vertically sliding plate 220. Horizontally sliding plate 215 slides along grooves 225 in housing 230, via rails 235. Vertically sliding plate 220 is retained in U-shaped housing 230 by a ridge 240, but is free to travel upwards along the inside edge 245 of housing 230. Vertically sliding plate 220 has a push plate 250 connected to it by springs 255. By pushing on push plate 250 the plates 215 and 220 can be resiliently biased together. In this way a user may apply pressure to the underside of vertically sliding plate 220 by pushing on push plate 250. As can be appreciated from FIGS. 8–11, horizontally sliding plate 215 and vertically sliding plate 220 move along substantially orthogonal directions.

In the operation of the device, a stent carrying catheter 260 is placed in between plates 220 and 215, with catheter 260 entering through slot 265, and facing transverse to the direction of movement of horizontally sliding plate 215. Thereinafter, horizontally sliding plate 215 is moved relative to vertically sliding plate 220, to compress the stent about the catheter. As can be seen from the drawings, horizontally sliding plate 215 is constrained by grooves 225 to move along a single direction relative to vertically sliding plate 220.

As before, a force measuring transducer and suitable output may be placed in either or both of plates 215 and 220 to measure the force imparted to the stent carrying catheter and indicate the results.

The embodiment of FIGS. 8–11 is sized to fit into a user's palm. The horizontally sliding plate 215 can be reciprocated with a thumb while housing 230 is held in the user's palm, and the user's fingers can apply pressure to push plate 250 affixed to the underside of vertically sliding plate 220. Springs 255 oppose the force of the user's fingers. In this way feedback can be experienced by the user.

While in the preferred embodiment the stent described is intended to be an intraluminal vascular prosthesis for use within a blood vessel, and the balloon delivery catheter is of the kind used in therapeutic coronary angioplasty, it will be appreciated by those skilled in the art that modifications may be made to the present invention to allow the present invention to be used to load any type of prosthesis. The present invention is not limited to stents that are deployed in a patient's vasculature but has wide applications to loading any type of graft, prosthesis, liner or similar structure. Furthermore, the stent may be delivered not only into coronary arteries but into any body lumen. Other modifications can be made to the present invention by those skilled in the art without departing from the scope thereof.

What is claimed is:

1. A method of affixing an intravascular stent onto a catheter, comprising:

placing an intravascular stent onto a catheter, placing the portion of said catheter containing said stent between two substantially flat surfaces, providing relative sliding movement between said two substantially flat surfaces and simultaneously imparting compressive forces on said stent to removably attach said stent onto the catheter.

2. The method of affixing an intravascular stent onto a catheter according to claim 1, wherein said two substantially flat surfaces are slidably moved along two directions.

3. The method of affixing an intravascular stent onto a catheter according to claim 2, wherein said two substantially flat surfaces are moved along two substantially orthogonal directions.

4. The method of affixing an intravascular stent onto a catheter according to claim 1, further comprising measuring and displaying said compressive force applied to compress said stent onto said catheter.

5. The method of affixing an intravascular stent onto a catheter according to claim 1, wherein said step of providing relative sliding movement between said two substantially flat surfaces includes the step of providing movement of one of said substantially flat surfaces while maintaining the other substantially flat surface stationary.

6. The method of affixing an intravascular stent onto a catheter according to claim 1, wherein said two substantially flat surfaces remain substantially parallel while mounting said stent on said catheter.

\* \* \* \* \*